US010170291B1

(12) United States Patent
Hsu et al.

(10) Patent No.: US 10,170,291 B1
(45) Date of Patent: Jan. 1, 2019

(54) APPARATUS FOR ON-LINE MONITORING PARTICLE CONTAMINATION IN SPECIAL GASES

(71) Applicant: Industrial Technology Research Institute, Hsinchu (TW)

(72) Inventors: I-Hsiang Hsu, Kaohsiung (TW); Fang-Hsin Lin, Taichung (TW); Yi-Hung Liu, Taipei (TW); Chun-Ling Chang, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 15/836,940

(22) Filed: Dec. 11, 2017

(30) Foreign Application Priority Data

Oct. 19, 2017 (TW) .............................. 106135875 A (51) Int. Cl.
*H01J 49/10* (2006.01)
*H01J 49/04* (2006.01)

(52) U.S. Cl.
CPC ........ *H01J 49/0422* (2013.01); *H01J 49/105* (2013.01)

(58) Field of Classification Search
CPC ............................ H01J 49/0422; H01J 49/105
USPC ......................................... 250/281, 282, 288
See application file for complete search history.

(56) References Cited

U.S. PATENT DOCUMENTS

2011/0133074 A1   6/2011   Nakanishi et al.

FOREIGN PATENT DOCUMENTS

| CN | 103487494 | 1/2014 |
|----|-----------|--------|
| CN | 104677975 | 6/2015 |
| JP | H07500416 | 1/1995 |
| JP | 2006170659 | 6/2006 |
| JP | 2012008059 | 1/2012 |

OTHER PUBLICATIONS

Kohei Nishiguchi et al., "Real-time multielement monitoring of airborne particulate matter using ICP-MS instrument equipped with gas converter apparatus", Journal of Analytical Atomic Spectrometry, Jul. 2, 2008, pp. 1125-1129.
Yoshinari Suzuki et al., "Real-time monitoring and determination of Pb in a single airborne nanoparticle", Journal of Analytical Atomic Spectrometry, Jun. 4, 2010, pp. 947-949.
Kohei Nishiguchi et al., "Gas to Particle Conversion-Gas Exchange Technique for Direct Analysis of Metal Carbonyl Gas by Inductively Coupled Plasma Mass Spectrometry", Analytical Chemistry, Sep. 23, 2014, pp. 10025-10029.

(Continued)

*Primary Examiner* — Nicole Ippolito
*Assistant Examiner* — Hanway Chang
(74) *Attorney, Agent, or Firm* — JCIPRNET (57) ABSTRACT

An apparatus for on-line monitoring particle contamination in special gas includes a single particle inductively coupled plasma mass spectrometry (sp-ICPMS) and a gas exchange device (GED). The gas exchange device is coupled to the sp-ICPMS. The gas exchange device includes a corrosion resistant outer tube and a polytetrafluoroethylene (PTFE) inner tube. A gap is formed between the corrosion resistant outer tube and the PTFE inner tube. The length of the PTFE inner tube is 1 meter or more. The argon gas flows in the gap, and the special gas flow in the PTFE inner tube.

12 Claims, 7 Drawing Sheets

(56) References Cited

OTHER PUBLICATIONS

Masaki Ohata and Kohei Nishiguchi, "Direct analysis of gaseous mercury in ambient air by gas to particle conversion-gas exchange ICPMS", Journal of Analytical Atomic Spectrometry, Feb. 20, 2017, pp. 1-32.

Masaki Ohata et al., "Direct analysis of ultra-trace semiconductor gas by inductively coupled plasma mass spectrometry coupled with gas to particle conversion-gas exchange technique", Analytica Chimica Acta, Sep. 2015, pp. 73-78.

J-Science Lab Co. Ltd., "Gas Exchange Device", Aug. 12, 2016, Available at: http://j-sl.com/resources/pdf/products/ged-pamphlet2015-jp.pdf.

J-Science Lab Co. Ltd., "Gas Exchange Device, Standard GED-01", Nov. 3, 2015, Available at: http://j-sl.com/products/gas/ged-01-en.php.

"Office Action of Taiwan Counterpart Application", dated May 14, 2018, p. 1-p. 6.

APPARATUS FOR ON-LINE MONITORING PARTICLE CONTAMINATION IN SPECIAL GASES

CROSS-REFERENCE TO RELATED APPLICATION

This application claims the priority benefit of Taiwan application serial no. 106135875, filed on Oct. 19, 2017. The entirety of the above-mentioned patent application is hereby incorporated by reference herein and made a part of this specification.

TECHNICAL FIELD

The disclosure relates to an apparatus for on-line monitoring particle contamination in special gases.

BACKGROUND

During fabrication of a semiconductor, the use of special gases is usually required for different processes. For example, $NH_3$ and $SiH_2Cl_2$ are employed as raw materials for forming a silicon nitride layer, $NH_3$ and $O_2$ are employed for wafer cleaning, HF is used for etching silicon dioxide ($SiO_2$), and so on. However, if these special gases contain metal particles, even though in a very small amount, the metal particles may possibly fall on a surface of an object to be processed and cause yield loss.

Therefore, online monitoring particle contamination in a conveying gas becomes a great challenge. Recently, there are commonly used apparatuses for monitoring particle contamination, e.g., a scanning mobility particle sizer (SMPS) or a fast mobility particle sizer (FMPS); however, as long as a particle size is smaller than a nanometer degree, collection efficiency thereof will be reduced down to 20% or less.

Therefore, a detection technique using a single particle inductively coupled plasma mass spectrometry (sp-ICPMS) is currently developed. Nevertheless, such detection technique is not yet actually applied online, and no researches for the monitoring of the particle contamination in special gases are conducted.

SUMMARY

The disclosure introduces an apparatus for on-line monitoring particle contamination in a special gas including a single particle inductively coupled plasma mass spectrometry (sp-ICPMS) coupled a gas exchange device (GED). The gas exchange device includes a corrosion resistant outer tube and a polytetrafluoroethylene (PTFE) inner tube. The PTFE inner tube is disposed inside the corrosion resistant outer tube, a gap is formed between the corrosion resistant outer tube and the polytetrafluoroethylene (PTFE) inner tube, and a length of the PTFE inner tube is 1 meter or more. The gap is applied for flowing an argon gas, and the PTFE inner tube is applied for flowing the special gases.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Embodiments are provided below and described in detail with reference to the accompanying drawings; however, the illustrated embodiments construe no limitations to the scope of the disclosure. In addition, the drawings are provided for illustrative purpose and are not illustrated in accordance with the original sizes, in which different components may be exaggerated or shrunk for being displayed in one drawing. In addition, for comprehensive convenience, the same components will be labeled by the same symbols hereinafter. Moreover, terms such as "comprise", "include", "have", "contain" and so on which are employed herein, are all open terms, i.e., contain but not are limited to.

Figure 1:
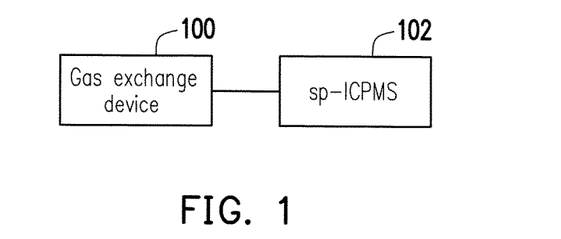
FIG. 1 is a functional block diagram illustrating an apparatus for on-line monitoring particle contamination in special gases according to an embodiment of the disclosure.

FIG. 1 is a functional block diagram illustrating an apparatus for on-line monitoring particle contamination in special gases according to an embodiment of the disclosure.

Referring to FIG. 1, an apparatus for on-line monitoring particle contamination in special gases includes a gas exchange device 100 and a single particle inductively coupled plasma mass spectrometry (sp-ICPMS) 102, and the gas exchange device 100 is coupled to the sp-ICPMS 102. In the present embodiment, the sp-ICPMS 102 may be an existing sp-ICPMS, in which a gas input from the gas exchange device 100 is nebulized, such that particles or aerosols contained therein are guided into an inductively coupled plasma (not shown), which are dissociated and ionized and then enter the mass spectrometry for detection.

In the disclosure, a method of quantifying a particle mass includes establishing a calibration curve by using a metal element standard, thereby obtaining an equation expressing the relation between a metal element mass and a measurement signal, after the particles enter the sp-ICPMS 102, operating the relation equation by using the obtained signal value to obtain a particle mass, and obtaining a particle size of the particles by Formula (1) below.

$$d = \sqrt[3]{\frac{6 * W_p}{\rho * \pi}} \qquad (1)$$

In Formula (1), d represents a particle size, $W_p$ represents a mass transmitted within an integration time, and $\rho$ represents a particle density. A particle quantity concentration is employed to calculate counts of measured signals, where a signal represents a particle, and the particle quantity concentration may be obtained by calculating Formula (2) below.

$$C_{NP} = \frac{f}{Q * \eta * t} \qquad (2)$$

In Formula (2), $C_{NP}$ represents a particle quantity concentration, f represents the measured number of the particles, Q represents an introduction velocity of a sample, $\eta$ represents a transmission efficiency, and t represents a total measurement time.

Figure 2:
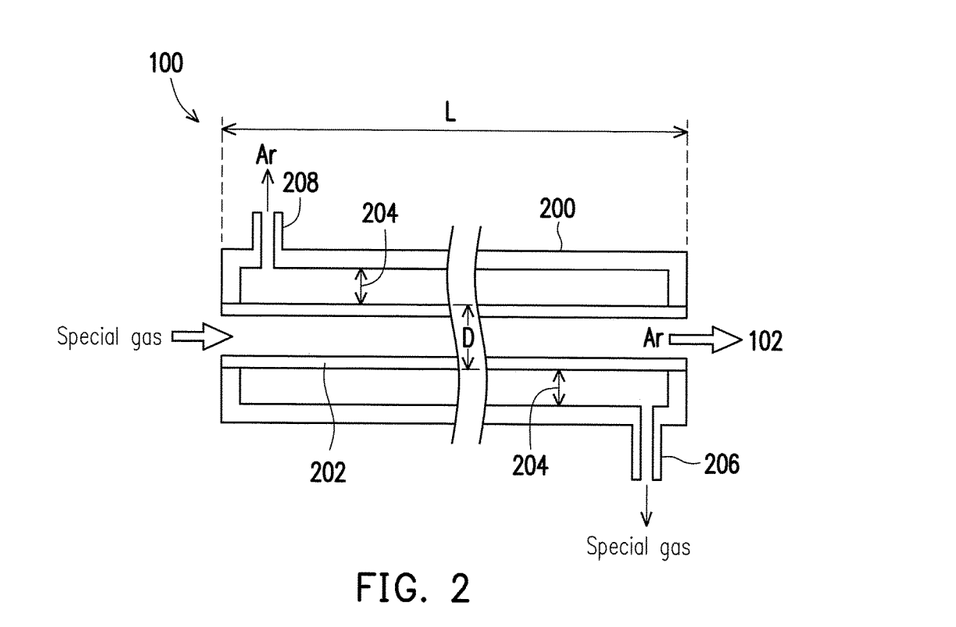
FIG. 2 is a schematic illustrating an example of the gas exchange device depicted in FIG. 1.

FIG. 2 is a schematic illustrating an example of the gas exchange device depicted in FIG. 1.

In FIG. 2, the gas exchange device 100 includes a corrosion resistant outer tube 200 and a polytetrafluoroethylene (PTFE) inner tube 202 disposed inside the corrosion resistant outer tube 200. A gap 204 is formed between the corrosion resistant outer tube 200 and the PTFE inner tube 202. A material of the corrosion resistant outer tube 200 includes, for example, a PTFE tube or a stainless steel tube with a surface treated with PTFE, and a length L1 of the PTFE inner tube 202 is 1 meter or more. In the present embodiment, an argon gas flows in the gap 204, a special gas flows in the PTFE inner tube 202, and a ratio of a flow rate of the special gas in the PTFE inner tube 202 to a flow rate of the argon gas in the gap 204 is, for example, ½ or less. Thus, with the PTFE inner tube 202 having the length of 1 meter or more, the special gas is completely exchanged for the argon gas, and accordingly the gas free of the special gas enters the sp-ICPMS 102. The special gas includes $NH_3$, HCl, $NF_3$, $CO_2$, $N_2O$, $BF_3$, $AsH_3$, $PH_3$, $GeH_4$, $CF_4$ or HF which is toxic or may cause the plasma in the sp-ICPMS 102 to be instable.

FIG. 2 further illustrates the argon gas provided through a gas inlet tube 206 and the special gas exhausted from the gas outlet tube 208. From a perspective of increasing a rate of gas exchange, the PTFE inner tube 202 has a porosity of, for example, 50% to 70%, and a pore size of the PTFE inner tube 202 is, for example, between 200 nm and 500 nm. Thus, the special gas entering PTFE inner tube 202 and metal particles (not shown) carried thereby may encounter an effect that the special gas permeates to the gap 204 through the pores of the PTFE inner tube 202 and exchanges for the argon gas in the gap 204, while the metal particles still stay in the PTFE inner tube 202.

Figure 3:
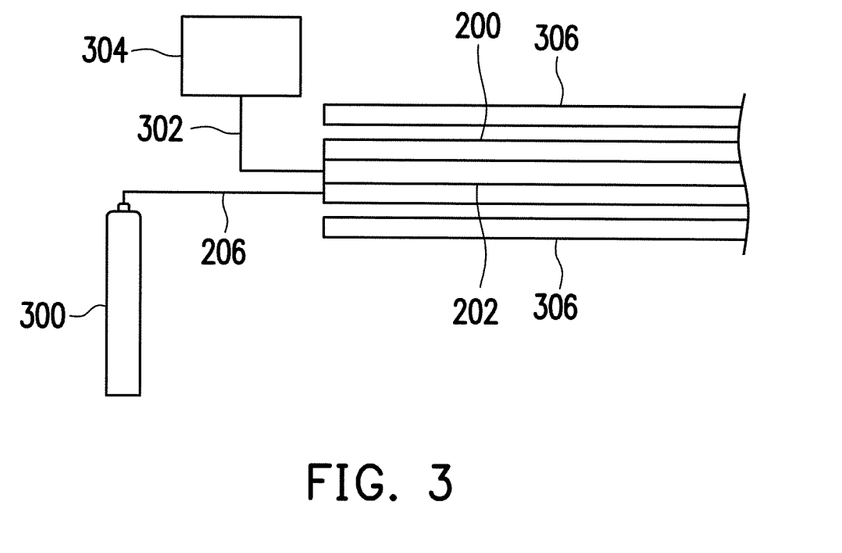
FIG. 3 is a schematic illustrating another example of the gas exchange device depicted in FIG. 1.

FIG. 3 is a schematic illustrating another example of the gas exchange device depicted in FIG. 1, in which some of the elements are omitted for clarity.

In FIG. 3, the argon gas is supplied to the gap between the corrosion resistant outer tube 200 and the PTFE inner tube 202 from a gas supply device 300 (for example, a gas cylinder) connected with the gas inlet tube 206. The special gas is supplied into the PTFE inner tube 202 through a gas pipeline 302. Meanwhile, the special gas may be first stored in a collection device 304, or alternatively, the special gas under test is directly transmitted from a machine (not shown) into the PTFE inner tube 202. Additionally, in order to prevent the special gas from being condensed in the tube and to increase the rate of gas exchange, the corrosion resistant outer tube 200 may be additionally disposed with a heating device 306 for increasing the temperature inside the corrosion resistant outer tube 200.

Figure 4A:
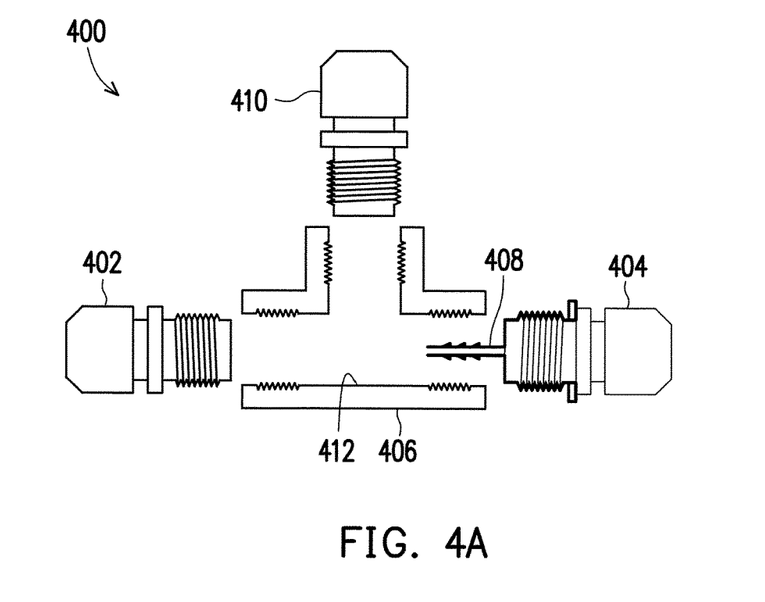
FIG. 4A is an exploded diagram illustrating an example of an adaptor device for the apparatus depicted in FIG. 1.
Figure 4B:
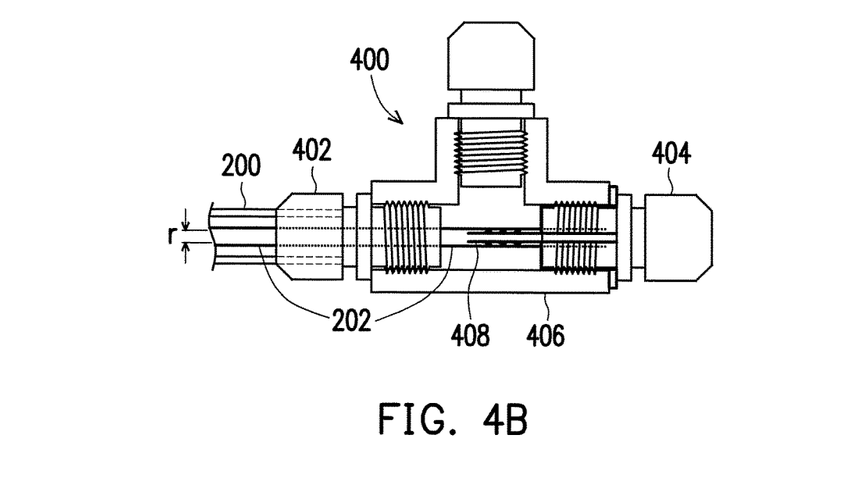
FIG. 4B is an assembly diagram of the adaptor device depicted in FIG. 4A.

In addition, the apparatus for on-line monitoring particle contamination in special gas of the present embodiment, an adaptor device may be additionally disposed, as illustrated in FIG. 4A and FIG. 4B, to prevent the special gas which has causticity and is harmful to biological environment from leaking.

FIG. 4A and IG. 4B are respectively an exploded diagram and an assembly diagram of an adaptor device for the apparatus depicted in FIG. 1. Referring first to FIG. 4A, an adaptor device 400 at least includes a first connector 402, a second connector 404 and an adaptor 406 located between the first and the second connectors 402 and 404. A long-tail connector is further disposed inside the second connector 404 to serve as an inner/outer tube leakproof connector 408 with its long-tail end disposed facing the first connector 402. An inner surface 412 of the adaptor 406 is entirely plated with a teflon film to avoid being rusted when the special gas is employed. In addition, for safety, a third connection 410 may be additionally disposed in the adaptor device 400 to serve as a leakproof connecter for connecting with an exhaustion apparatus (not shown).

The adaptor device 400, when being employed in the apparatus of the present embodiment, is disposed between the gas exchange device 100 and the sp-ICPMS 102 illustrated in FIG. 1. The first connector 402 may be coupled to the gas exchange device, and the second connector 404 may be may be coupled to the sp-ICPMS.

Referring to FIG. 4B, the corrosion resistant outer tube 200 and the PTFE inner tube 202 are locked to the first connector 402, and the PTFE inner tube 202 extends into the adaptor 406 and is engaged tightly with the PTFE inner tube 202 by the inner/outer tube leakproof connector 408. Thus, even though a great pressure change occurs in the PTFE inner tube 202, the special gas is not leaked out.

In FIG. 4B, an outer diameter of the long-tail end of the inner/outer tube leakproof connector 408 is approximately equal to an inner diameter r of the PTFE inner tube 202, but the invention is not limited thereto.

With the disposition of the adaptor device 400, an effect of preventing the special gas which is toxic and harmful to the environment from leaking may be further achieved. Likewise, the adaptor device 400 may also be disposed among the gas pipeline 302, the corrosion resistant outer tube 200 and the PTFE inner tube 202. For example, the gas pipeline 302 is connected with the second connector 402 and the inner/outer tube leakproof connector 408, and the first connector 402 is connected with the corrosion resistant outer tube 200 and the PTFE inner tube 202.

Figure 5:
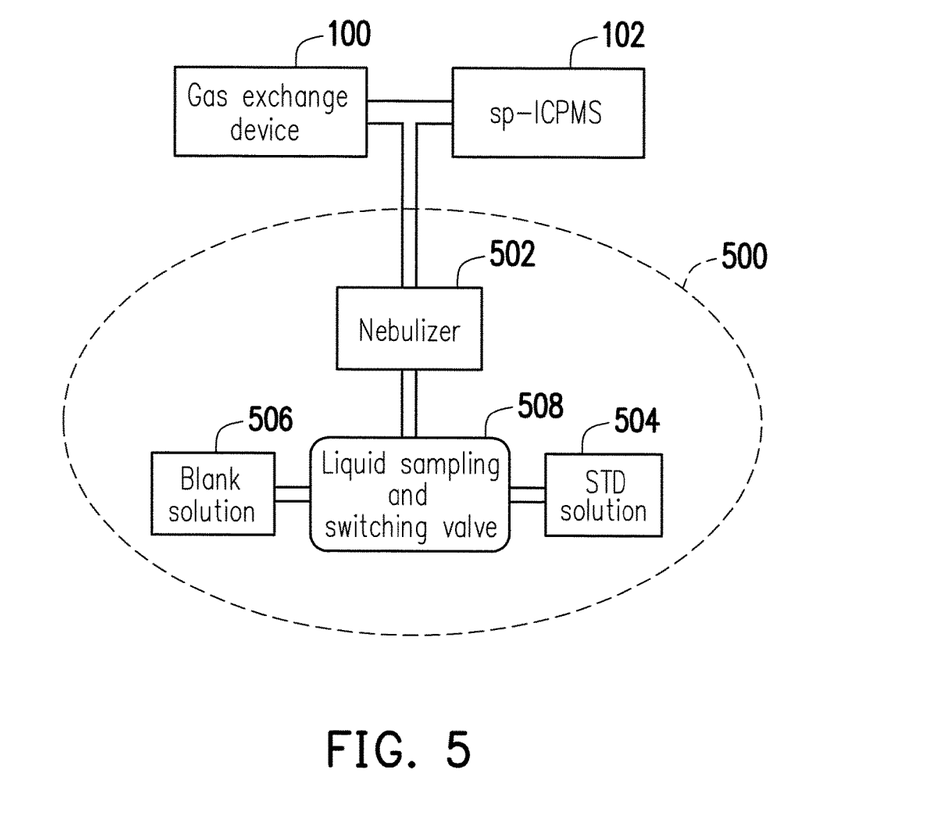
FIG. 5 is a schematic diagram illustrating an apparatus for on-line monitoring particle contamination in special gases according to another embodiment of the disclosure.

FIG. 5 is a schematic diagram illustrating an apparatus for on-line monitoring particle contamination in special gases according to another embodiment of the disclosure, where element labels and portions content related to the previous embodiment are referenced hereafter, the same or similar elements are indicated by the same or similar reference labels, and the descriptions of the same technical details are therefore not repeated here. The parts omitted from description may be referenced from the afore-described embodiments and will not be repeated in the embodiment below.

In FIG. 5, the apparatus for on-line monitoring particle contamination in special gases, besides the gas exchange device 100 and the sp-ICPMS 102, further includes a standard introduction device 500. The standard introduction device 500 is connected between the gas exchange device 100 and the sp-ICPMS 102 and employed to quantify a mass of the particles entering the sp-ICPMS 102. For example, the standard introduction device 500 may have a nebulizer 502 and a liquid sampling and switching valve 508 which is connected with a blank solution 506 and a STD (standard) solution 504. The type of the solution transmitted to the nebulizer 502 may be selected by controlling the liquid sampling and switching valve 508. Thus, the nebulizer 502 may nebulize the STD solution containing metal elements in different concentrations into microdroplets, and the microdroplets are then sent into the sp-ICPMS 102 for measurement. In this way, a relation diagram showing the relation between concentration and signal intensity is established, and a relation equation for quantifying a mass of the particles in the special gas is obtained by means of linear regression, so as to achieve a quantification effect. In this case, the nebulizer 502 may be a pneumatic nebulizer operated together with a cyclonic spray chamber, an ultrasonic nebulizer or a single microdroplet generation device.

Experiment examples are provided below for demonstrating effects that may be achieved by the disclosure; however, the disclosure is not limited to the contents set forth below.

Experiment Example 1

Figure 6A:
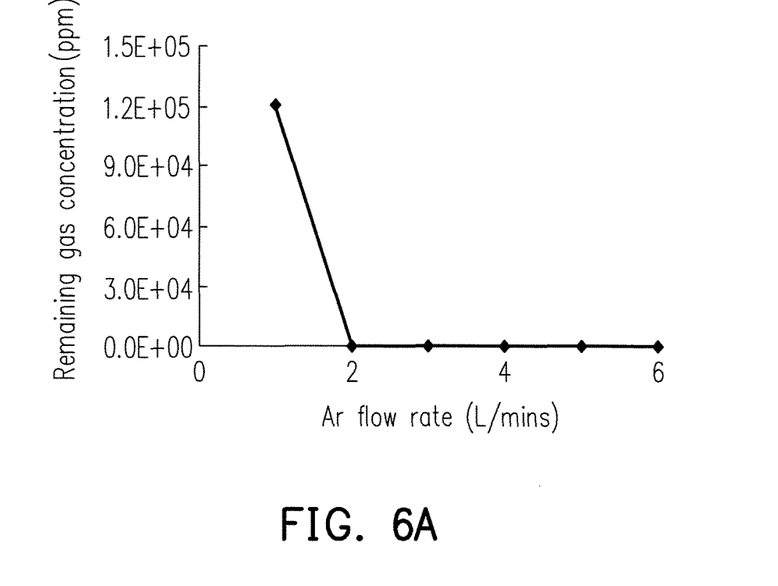
FIG. 6A is a graph showing curves illustrating the relationships between a gas concentration of $NH_3$ and an argon flow rate of Experiment Example 1.

In this experiment example, the gas exchange device as illustrated in FIG. 2 is employed, a length of the PTFE inner tube is 1 meter, the PTFE inner tube has a porosity of 50% to 70%, and a pore size of the PTFE inner tube is approximately between 200 nm and 500 nm. Then, $NH_3$ is supplied from an end of the PTFE inner tube 202, an argon gas is supplied into the gap between the inner tube and the outer tube, a flow rate of $NH_3$ is fixed at 1 L/minute, and a flow rate of argon gas is controlled by using a mass flow meter, which is then measured by a Fourier transform infrared spectrometer. As the argon flow rate changes, a gas concentration of $NH_3$ of the other end (an output end) of the PTFE inner tube is measured to obtain exchange ratios of the gas in the inner tube/the gas in the outer tube in different scenarios, of which results are shown in FIG. 6A.

Experiment Example 2

Figure 6B:
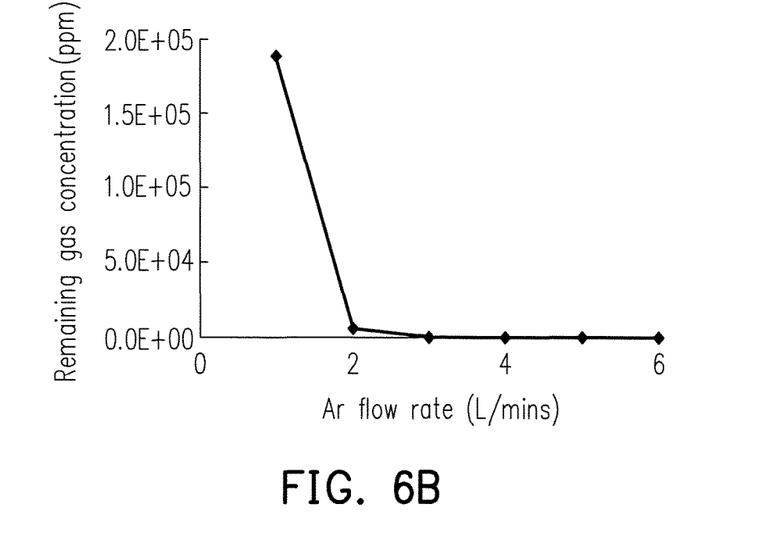
FIG. 6B is a graph showing curves illustrating the relationships between a gas concentration of $N_2O$ and an argon flow rate of Experiment Example 2.

In this experiment example, the same apparatus employed in Experiment Example 1 is also employed to perform the same measurement on $N_2O$, of which results are shown in FIG. 6B.

Experiment Example 3

Figure 6C:
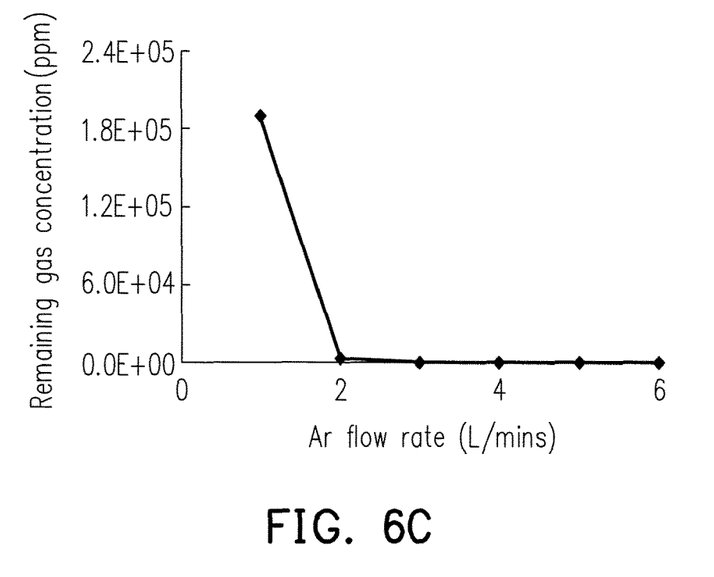
FIG. 6C is a graph showing curves illustrating the relationships between a gas concentration of $CO_2$ and an argon flow rate of Experiment Example 3.

In this experiment example, the same apparatus employed in Experiment Example 1 is also employed to perform the same measurement on $CO_2$, of which results are shown in FIG. 6C.

Experiment Example 4

Figure 6D:
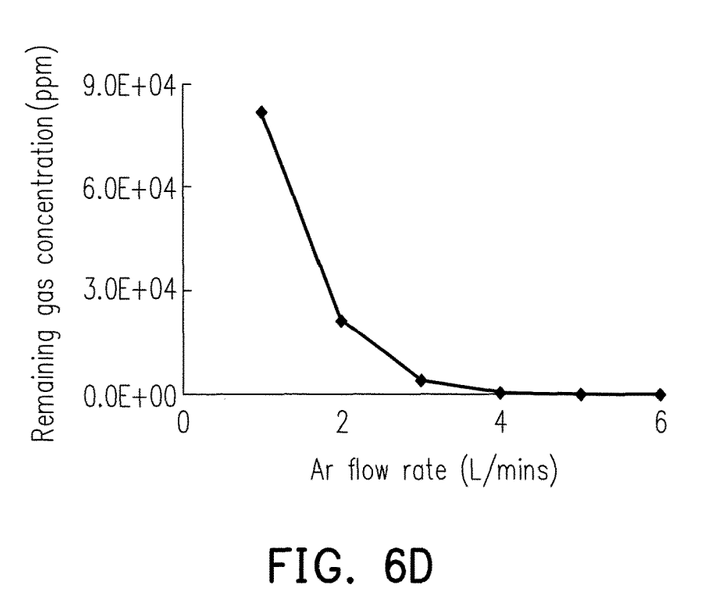
FIG. 6D is a graph showing curves illustrating the relationships between a gas concentration of $CF_4$ and an argon flow rate of Experiment Example 4.

In this experiment example, the same apparatus employed in Experiment Example 1 is also employed to perform the same measurement on $CF_4$, of which results are shown in FIG. 6D.

According to FIG. 6A to FIG. 6D, in a scenario where the ratio of the special gas flow rate to the argon flow rate is, for example, 1:2 or more, the remaining gas concentration in each example is dramatically reduced, i.e., the exchange ratios are all greater than 99%, such that the result of gas exchange can be effectively achieved.

Experiment Example 5

Figure 7:
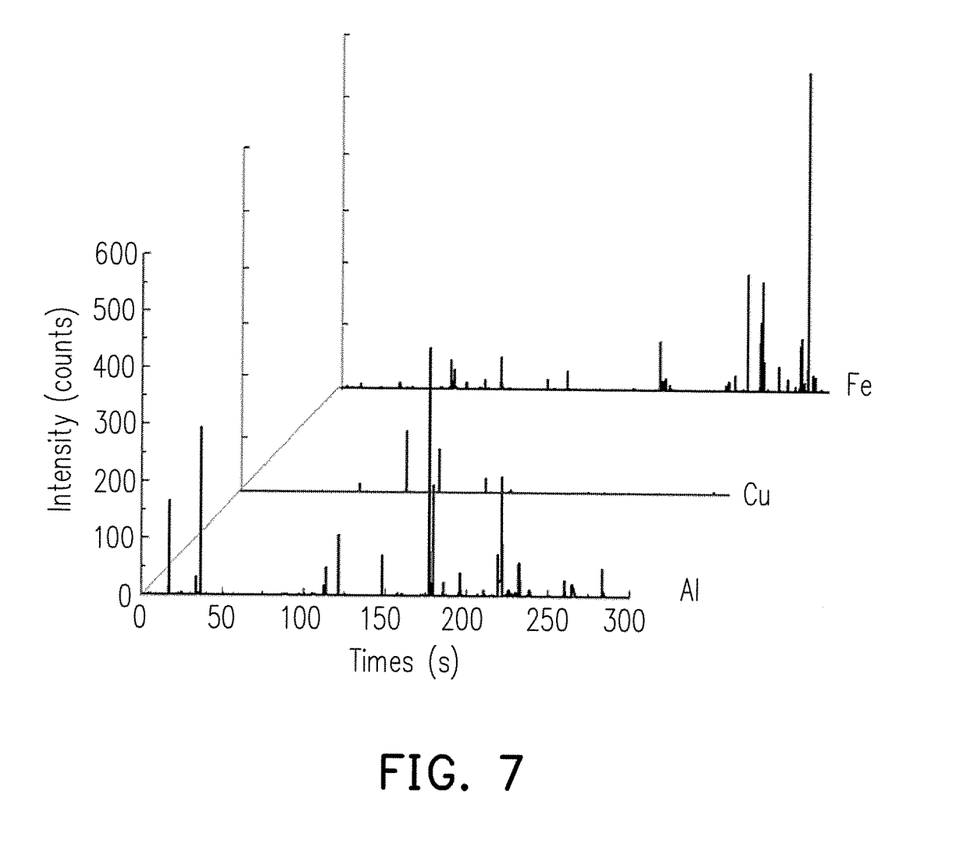
FIG. 7 is a component analysis diagram of Experiment Example 5.

In this experiment example, the gas exchange device and the sp-ICPMS illustrated in FIG. 1 is employed to measure metal particle contamination in the $NH_3$ gas. Regarding the gas exchange device, the $NH_3$ flow rate is fixed at 1 L/minute, the argon flow rate is fixed at 2 L/minute, the outlet end of the inner tube of the gas exchange device is connected into the sp-ICPMS through a connection tube, a measurement time of the sp-ICPMS is set to 5 minutes, and various elements, such as Al, Cu, Fe and so on, are selected, thereby obtaining instant data as illustrated in FIG. 7.

Experiment Example 6

The apparatus employed in Experiment Example 1 is employed for gas exchange for the $NH_3$ gas, the exchanged gas is sent through a connection tube with one end connected with the sp-ICPMS and another end connected with the nebulizer, and the entire experiment architecture is like that as illustrated in FIG. 5. The nebulizer is employed to nebulize the liquid element standard into aerosols, which are sent into the sp-ICPMS for measurement. Concentrations of the element standard in use are 0, 100 and 200 ng/kg, and an element calibration curve may be obtained according to the concentrations and obtained signal values. By substituting each signal value obtained in FIG. 7 into the calibration curve, an element mass may be obtained, the element mass may be converted into a particle diameter through Formula (1) set forth above, and the concentration is a sum of each measured element mass divided by an introduction mass of $NH_3$, of which results are shown in Table 1 below.

TABLE 1

| Element | Density (g/cm$^3$) | LOD (nm) | <100 nm (Numbers) | 100-500 nm (Numbers) | >500 nm (Numbers) | Concentration (ng/g) |
|---------|---------|------|---------|---------|---------|---------|
| Na | 0.96 | 19.2 | — | 2 | — | 1.4 |
| Mg | 1.73 | 5.1 | — | 9 | 1 | 25.0 |
| Al | 2.70 | 7.9 | — | 83 | 4 | 217.0 |
| K | 0.86 | 25.3 | — | 8 | — | 7.7 |
| Fe | 7.87 | 12.8 | 11 | 75 | — | 105.4 |
| Ni | 8.91 | 9.0 | — | — | — | ND |
| Cu | 8.96 | 5.7 | — | 54 | — | 54.8 |
| Zn | 7.14 | 7.4 | — | — | — | ND |
| Cr | 19.3 | 3.7 | — | — | — | ND |

*ND indicates that the value is less than a minimum scale of the apparatus.

According to Table 1, a particle diameter distribution of each element contained in $NH_3$ and a total concentration thereof may be obtained, where the particle diameter distributions mainly fall within a range from 100 to 500 nm, and among the elements, Al and Fe have the greater total numbers of particles and the greater concentrations as well. Accordingly, by employing the sp-ICPMS in cooperation with the gas exchange device, quantifying and monitoring particle contamination in the special gases can be successfully achieved.

In light of the foregoing, in the disclosure, the sp-ICPMS is operated in cooperation with the gas exchange device including the inner and the outer tubes. The inner tube is designed with a specific material and size and therefore, can contribute to significantly increasing the rate of gas exchange and monitoring the special gases. In addition, with the specially designed adaptor device, the overall gas exchange device is capable of pressure withstanding, adaptive for monitoring the special gas and free from security concerns. Moreover, the standard introduction device can be further employed to achieve direct quantification and monitor of the samples after the gas exchange.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An apparatus for on-line monitoring particle contamination in a special gas, comprising:
   a single particle inductively coupled plasma mass spectrometry (sp-ICPMS); and
   a gas exchange device, coupled to the sp-ICPMS and comprising:
      a corrosion resistant outer tube; and
      a polytetrafluoroethylene (PTFE) inner tube, disposed inside the corrosion resistant outer tube, a gap being formed between the corrosion resistant outer tube and the PTFE inner tube, and a length of the PTFE inner tube being 1 meter or more, wherein
      the gap is applied for flowing an argon gas, and the PTFE inner tube is applied for flowing the special gas.

2. The apparatus as recited in claim 1, wherein the argon gas is supplied into the gap between the corrosion resistant outer tube and the PTFE inner tube by a gas supply device.

3. The apparatus as recited in claim 1, wherein the special gas is supplied into the PTFE inner tube through a gas pipeline.

4. The apparatus as recited in claim 1, wherein the PTFE inner tube has a porosity of 50% to 70%.

5. The apparatus as recited in claim 1, wherein a pore size of the PTFE inner tube is between 200 nm and 500 nm.

6. The apparatus as recited in claim 1, wherein the special gas comprises $NH_3$, HCl, $NF_3$, $CO_2$, $N_2O$, $BF_3$, $AsH_3$, $PH_3$, $GeH_4$, $CF_4$ or HF.

7. The apparatus as recited in claim 1, wherein a ratio of a flow rate of the special gas in the PTFE inner tube to a flow rate of the argon gas in the gap is ½ or less.

8. The apparatus as recited in claim 1, wherein a material of the corrosion resistant outer tube comprises PTFE or stainless steel with a surface treated with PTFE.

9. The apparatus as recited in claim 1, further comprising an adaptor device, disposed between the gas exchange device and the sp-ICPMS, wherein the adaptor device comprises:
   a first connector, coupled to the gas exchange device;
   a second connector, coupled to the sp-ICPMS;
   an adaptor, located between the first connector and the second connector; and
   an inner/outer tube leakproof connector, disposed inside the second connector, wherein the inner/outer tube leakproof connector is a long-tail connector engaged tightly with the PTFE inner tube.

10. The apparatus as recited in claim 9, wherein an outer diameter of a long-tail end of the long-tail connector is equal to an inner diameter of the PTFE inner tube.

11. The apparatus as recited in claim 9, wherein an outer diameter of a long-tail end of the long-tail connector is greater than an inner diameter of the PTFE inner tube and less than an outer diameter of the PTFE inner tube.

12. The apparatus as recited in claim 1, further comprising: a standard introduction device, connected between the gas exchange device and the sp-ICPMS and employed to quantify a flow rate of a gas entering the sp-ICPMS.

* * * * *